(12) United States Patent
Kim et al.

(10) Patent No.: US 7,740,880 B2
(45) Date of Patent: Jun. 22, 2010

(54) POLYMERIC CARRIER FOR DELIVERY OF SMALL INTERFERING RNA

(75) Inventors: Won Jong Kim, Salt Lake City, UT (US); Sung Wan Kim, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 736 days.

(21) Appl. No.: 11/367,228

(22) Filed: Mar. 3, 2006

(65) Prior Publication Data

US 2007/0207966 A1    Sep. 6, 2007

(51) Int. Cl.
*A61K 9/127* (2006.01)
*A61K 31/70* (2006.01)
*A01N 43/04* (2006.01)

(52) U.S. Cl. .................... 424/450; 514/44
(58) Field of Classification Search ............. None
See application file for complete search history.

(56) References Cited

U.S. PATENT DOCUMENTS

2005/0215497 A1 * 9/2005 Harel-Bellan et al. ........ 514/44

FOREIGN PATENT DOCUMENTS

WO    WO02069930 A1 *    9/2002

OTHER PUBLICATIONS

Futaki et al. Bioconjugate Chemistry, 2001, vol. 12, pp. 1005-1011.*
P. A. Wender et al., The design, synthesis, and evaluation of molecules that enable or enhance cellular uptake: Peptoid molecular transporters, 97 Proc. Nat'l Acad. Sci. USA 13003-13008 (2000).
S. Futaki et al., Arginine-rich Peptides, 276 Journal of Biological Chemistry 5836-5840 (2001).
S. Futaki et al., Stearylated Arginine-Rich Peptides: A New Class of Transfection Systems, 12 Bioconjugate Chem 1005-1011 (2001).

* cited by examiner

*Primary Examiner*—Janet L Epps-Smith
(74) *Attorney, Agent, or Firm*—Clayton, Howarth & Cannon, P.C.

(57) ABSTRACT

A carrier for delivering small interfering RNA (siRNA) into cells includes a cholesterol residue covalently bonded to oligoarginine. Mixing the siRNA with the carrier produces a complex-containing composition. Contacting a cell with the complex-containing composition results in delivery of the siRNA into the cell. Delivery of an siRNA targeted to vascular endothelial growth factor is a treatment for cancer. Methods of making the carrier and complex are also disclosed.

11 Claims, 8 Drawing Sheets

FIG. 3D siVEGF

5'-AUGUGAAUGCAGACCAAAGAATT-3'
3'-TTUACACUUACGUCUGGUUUCUU-5' scVEGF

5'-GAUAGCAAUGACGAAUGCGUATT-3'
3'-TTCUAUCGUUACUGCUUACGCAU-5'

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Top strand of siVEGF

<400> SEQUENCE: 1
augugaaugc agaccaaaga att                                              23

<210> SEQ ID NO 2
<211> LENGTH: 23
<212> TYPE: DNA
<213> ORGANISM: Artificial Sequence
<220> FEATURE:
<223> OTHER INFORMATION: Bottom strand of siVEGF

<400> SEQUENCE: 2
uucuuugguc ugcauucaca utt                                              23

<210> SEQ ID NO 3
<211> LENGTH: 23
<212> TYPE: DNA
<213> ORGANISM: Artificial Sequence
<220> FEATURE:
<223> OTHER INFORMATION: Top strand of scVEGF

<400> SEQUENCE: 3
gauagcaaug acgaaugcgu att                                              23

<210> SEQ ID NO 4
<211> LENGTH: 23
<212> TYPE: DNA
<213> ORGANISM: Artificial Sequence
<220> FEATURE:
<223> OTHER INFORMATION: Bottom strand of scVEGF

<400> SEQUENCE: 4
uacgcauucg ucauugcuau ctt                                              23

POLYMERIC CARRIER FOR DELIVERY OF SMALL INTERFERING RNA

STATEMENT REGARDING FEDERALLY SPONSORED RESEARCH OR DEVELOPMENT

This invention was made with government support under grant no. CA107070 from the National Institutes of Health. The government has certain rights in the invention.

CROSS-REFERENCE TO RELATED APPLICATIONS

Not applicable.

BACKGROUND OF THE INVENTION

This invention relates to delivery of small interfering RNAs (siRNAs) for disease treatment. More particularly, this invention relates to a hydrophobically modified oligoarginine for use in delivering siRNAs for treatment of a disease, such as cancer.

The phenomenon of RNA interference (RNAi) or post-transcriptional gene silencing (PTGS) is an evolutionarily conserved biological response to double-stranded RNA (dsRNA) for degradation of the sequence-specific homologous mRNA. RNAi is initiated by the dsRNA-specific endonuclease, Dicer, which promotes processive cleavage of long dsRNA into double-stranded fragments between 21-23 nucleotides long, termed small interfering RNAs (siRNAs), which bind to the RNA-induced silencing complex (RISC) that recognizes target mRNA to be degraded. P. D. Zamore, T. Tuschl, P. A. Sharp & D. P. Bartel, RNAi: double-stranded RNA directs the ATP-dependent cleavage of mRNA at 21 to 23 nucleotide intervals, 101 Cell 25-33 (2000); S. M. Elbashir, W. Lendeckel & T. Tuschl, RNA interference is mediated by 21- and 22-nucleotide RNAs, 15 Genes Dev. 188-200 (2001); J. B. Opalinska & A. M. Gewirtz, Nucleic-acid therapeutics: basic principles and recent applications, 1 Nat. Rev. Drug Discov. 503-514 (2002); S. M. Elbashir, J. Harborth, W. Lendeckel, A. Yalcin, K. Weber & T. Tuschl, Duplexes of 21-nucleotide RNAs mediate RNA interference in cultured mammalian cells, 411 Nature 494-498 (2001). Recently, it has become a useful tool for specific gene silencing and analysis of gene function.

To improve the efficiency of siRNA function, delivery systems need to be developed to effectively condense siRNA to small particles, thereby enhancing cellular uptake and protection from enzymatic degradation. Ideas based on polymeric delivery systems for plasmid DNA, J.-S. Kim, A. Maruyama, T. Akaike & S. W. Kim, In vitro gene expression on smooth muscle cells using a terplex delivery system, 47 J. Control. Rel. 51-59 (1997); S. Han, R. I. Mahato & S. W. Kim, Water-soluble lipopolymer for gene delivery, 12 Bioconjugate Chem. 337-345 (2001); D. Y. Furgeson, W. S. Chan, J. W. Yockman & S. W. Kim, Modified linear polyethylenimine-cholesterol conjugates for DNA complexation, 14 Bioconjugate Chem. 840-847 (2003); W. J. Kim et al., Soluble Flt-1 gene delivery using PEI-g-PEG-RGD conjugate for anti-angiogenesis, 106 J. Control. Rel. 224-234 (2005); J. H. Jeong et al., Anti-GAD antibody targeted non-viral gene delivery to islet beta cells, 107 J. Control. Rel. 562-570 (2005), have begun to facilitate development of siRNA delivery vehicles, J. C. Bologna, G. Dom, F. Natt & J. Weiler, Linear polyethylenimine as a tool for comparative studies of antisense and short double-stranded RNA oligonucleotides, 23 Nucleosides Nucleotides Nucleic Acids 1729-1731 (2003); B. Urban-Klein, S. Werth, S. Abuharbeid, F. Czubayko & A. Aigner, RNAi-mediated gene-targeting through systemic application of polyethylenimine (PEI)-complexed siRNA in vivo, 12 Gene Ther. 461-466 (2005). Therefore, enhancement of transfection efficiency in vitro and in vivo has progressed rapidly. In fact, numerous attempts to enhance siRNA function have been made based on cationic lipopeptide, N. Unnamalai, B. G. Kang & W. S. Lee, Cationic oligopeptide-mediated delivery of dsRNA for post-transcriptional gene silencing in plant cells, 566 FEBS 307-310 (2004), steroid and lipid conjugates of siRNA, C. Lorenz, P. Hadwiger, M. John, H.-P. Vornlocher & C. Unverzagt, Steroid and lipid conjugates of siRNAs to enhance cellular uptake and gene silencing in liver cells, 14 Bioorg. Med. Chem. Lett. 4975-4977 (2004); S. Spagnou, A. D. Miller & M. Keller, Lipidic carriers of siRNA: Differences in the formulation, cellular uptake, and delivery with plasmid DNA, 43 Biochemistry 13348-13356 (2004), and block copolymer-coated calcium phosphate nanoparticles, Y. Kakizawa, S. Furukawa & K. Kataoka, Block copolymer-coated calcium phosphate nanoparticles sensing intracellular environment for oligodeoxynucleotide and siRNA delivery, 97 Control. Rel. 345-356 (2004). Recently, to enhance cellular uptake and transfection efficiency, arginine-rich cell membrane permeable carrier peptides, such as human immunodeficiency virus (HIV-1) TAT and antennapedia, have been developed as gene delivery vehicles. C. Rudolph et al., Oligomers of the arginine-rich motif of the HIV-1 TAT protein are capable of transferring plasmid DNA into cells, 278 J. Biol. Chem. 11411-11418 (2003); D. S. Manickam, H. S. Bisht, L. Wan, G. Mao & D. Oupicky, Influence of TAT-peptide polymerization on properties and transfection activity of TAT/DNA polyplexes, 102 J. Control. Rel. 293-306 (2005). In cell culture, a conjugate of an antisense oligonucleotide and the antennapedia peptide inhibited the translation of amyloid precursor protein at a concentration of 40 nM. B. Allinquant, P. Hantraye, P. Mailleux, K. Moya, C. Bouillot & A. Prochiantz, Downregulation of amyloid precursor protein inhibits neurite outgrowth in vitro, 128 J. Cell Biol. 919-927 (1995). In a separate study, the antennapedia-peptide-conjugated oligonucleotide against Cu/Zn superoxide dismutase showed a 100-fold higher efficiency in culture than did the oligonucleotide itself. C. M. Troy, D. Derossi, A. Prochiantz, L. A. Greene & M. L. Shelanski, L. Downregulation of Cu/Zn superoxide dismutase leads to cell death via the nitric oxide-peroxynitrite pathway, 16 J. Neurosci. 253-261 (1996). Furthermore, arginine oligopeptides have been modified with several hydrophobic lipid molecules to enhance plasmid gene transfection. S. Futaki et al., Stearylated arginine-rich peptides: A new class of transfection systems, 12 Bioconjugate Chem. 1005-1011 (2001).

An effective water soluble lipopolymer carrier (WSLP) was made by combining the cationic headgroup of branched polyethylenimine (bPEI, MW=1.8 kDa) with a hydrophobic lipid anchor, cholesterol chloroformate. S. Han, R. I. Mahato & S. W. Kim, Water-soluble lipopolymer for gene delivery, 12 Bioconjugate Chem. 337-345 (2001). WSLP showed low cytotoxicity and enhanced transfection efficacy in vitro and in vivo. Id., J. W. Yockman, A. Maheshwari, S. Han & S. W. Kim, Tumor regression by repeated intratumoral delivery of water soluble lipopolymers/p2CMVmIL-12 complexes, 87 J. Control. Rel. 177-186 (2003). The effectiveness of WSLP over bPEI was due to the modification of the inherent structural DNA complex to enhance the interaction with plasma membrane and facilitate endosomal escape.

While prior art carriers and methods of use thereof are known and are generally suitable for their limited purposes, they possess certain inherent deficiencies that detract from their overall utility. For example, carriers that provide enhanced cellular uptake, improved inhibition of nucleolytic inactivation, and low cost are needed.

In view of the foregoing, it will be appreciated that providing an improved polymeric carrier for use as a carrier in siRNA delivery would be a significant advancement in the art.

BRIEF SUMMARY OF THE INVENTION

An illustrative embodiment of the invention comprises a method of delivering a small interfering RNA into a cell, the method comprising contacting the cell with a complex formed by mixing the small interfering RNA with a conjugate comprising a cholesterol residue covalently bonded to oligoarginine.

In this method, the oligoarginine typically comprises about 4 to 16 arginine residues, with about 9 arginine residues being exemplary. The arginine residues may be in the L form, the D form, or in a mixture of L and D forms. In one illustrative embodiment of the invention, the cholesterol residue is linked to the oligoarginine through a formate residue. In another illustrative embodiment of the invention, the small interfering RNA is targeted to vascular endothelial growth factor. An example of such a small interfering RNA is siVEGF (SEQ ID NO:1 and SEQ ID NO:2).

Another illustrative embodiment of the invention comprises a method of treating cancer, the method comprising administering a complex to a patient in need of treatment for cancer wherein the complex comprises (a) a small interfering RNA targeted to vascular endothelial growth factor, and (b) a conjugate comprising a cholesterol residue covalently bonded to oligoarginine.

Still another illustrative embodiment of the invention comprises the small interfering RNA, siVEGF (SEQ ID NO:1 and SEQ ID NO:2).

Yet another illustrative embodiment of the invention comprises a conjugate for use in delivering small interfering RNA, the conjugate comprising a cholesterol residue covalently bonded to oligoarginine.

Another illustrative embodiment of the invention comprises a method of making a cholesterol- and oligoarginine-containing conjugate, the method comprising reacting cholesterol chloroformate with oligoarginine, thereby forming an amide bond linking a cholesterol residue and the oligoarginine.

Still another illustrative embodiment of the invention comprises a method of making a complex, the method comprising mixing a small interfering RNA with a conjugate comprising a cholesterol residue covalently bonded to oligoarginine, thereby forming the complex.

Another illustrative embodiment of the invention comprises a composition comprising a mixture of a small interfering RNA and a conjugate comprising a cholesterol residue covalently bonded to oligoarginine.

BRIEF DESCRIPTION OF THE SEVERAL VIEWS OF THE DRAWINGS

FIGS. 5A and 5B show VEGF silencing with complexes of siRNAs (siVEGF and scVEGF) and various carriers in CT-26 cells.

DETAILED DESCRIPTION

Before the present polymeric carrier for siRNA delivery and methods of use and making are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the"

include plural referents unless the context clearly dictates otherwise. Thus, for example, reference to a complex containing "a conjugate" includes a mixture of two or more conjugates, reference to "an siRNA" includes reference to one or more of such siRNAs, and reference to "an oligoarginine" includes reference to a mixture of two or more oligoarginines.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "administering" and similar terms mean delivering the siRNA/carrier complex to the individual being treated such that the complex can contact the targeted cells, such as tumor cells. Thus, the composition can be administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

RNA has been used for several years to reduce or interfere with expression of targeted genes in a variety of systems. Although originally thought to require use of long double-stranded RNA (dsRNA) molecules, the active mediators of RNAi are now known to be short dsRNAs. Short single-stranded antisense RNA molecules were demonstrated to be effective inhibitors of gene expression more than a decade ago, but are susceptible to degradation by a variety of nucleases and are therefore of limited utility without chemical modification. Double-stranded RNAs are surprisingly stable and, unlike single-stranded DNA or antisense RNA oligonucleotides, do not need extensive modification to survive in tissue culture media or living cells.

Short interfering RNAs are naturally produced by degradation of long dsRNAs by Dicer, an RNase III class enzyme. While these fragments are usually about 21 bases long, synthetic dsRNAs of a variety of lengths, ranging from 18 bases to 30 bases, D.-H. Kim et al., Synthetic dsRNA dicer-substrates enhance RNAi potency and efficacy, 23 Nature Biotechnology 222-226 (2005), can be used to suppress gene expression. These short dsRNAs are bound by the RNA Induced Silencing Complex (RISC), which contains several protein components including a ribonuclease that degrades the targeted mRNA. The antisense strand of the dsRNA directs target specificity of the RISC RNase activity, while the sense strand of an RNAi duplex appears to function mainly to stabilize the RNA prior to entry into RISC and is degraded or discarded after entering RISC.

Chemically synthesized RNAi duplexes have historically been made as two 21-mer oligonucleotides that form a 19-base RNA duplex with two deoxythymidine bases added as 3'overhangs. S. M. Elbashir et al., Functional anatomy of siRNAs for mediating efficient RNAi in Drosophila melanogaster embryo lysate, 20 EMBO J. 6877-6888 (2001). Blunt 19-mer duplexes can also be used to trigger RNAi in mammalian systems. F. Czaudema, Structural variations and stabilizing modifications of synthetic siRNAs in mammalian cells, 31 Nucleic Acids Res. 2705-2716 (2003). These blunt duplexes, however, are generally less potent. Blunt duplexes can be effectively used for longer RNAs that are Dicer substrates. D.-H. Kim et al., supra. In this case, the duplex is processed by Dicer to 21-mer length with 2-base 3'-overhangs before entry into RISC.

Figure 4A:
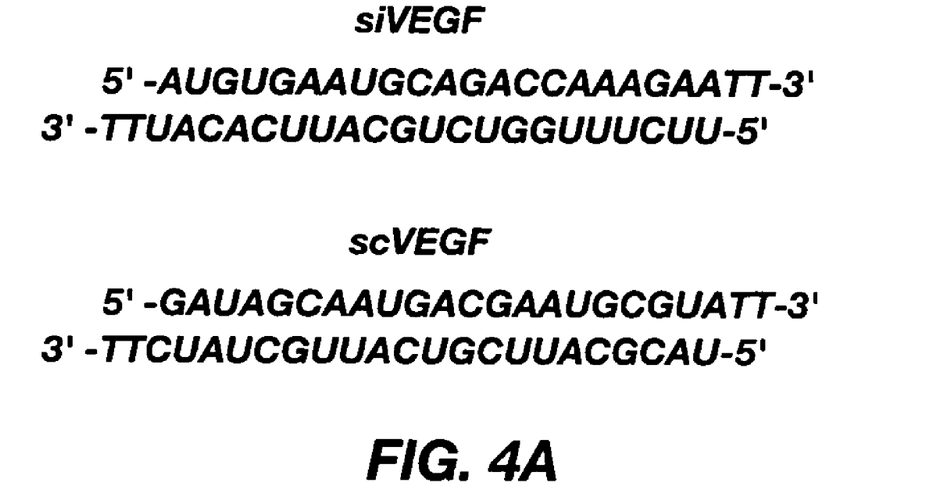
FIGS. 4A and 4B show sequences of siRNA targeting VEGF (siVEGF; SEQ ID NO:1 and SEQ ID NO:2) and scrambled VEGF siRNA (scVEGF; SEQ ID NO:3 and SEQ ID NO:4) (FIG. 4A), and electrophoretic patterns of siRNA complexes with Chol-R9 conjugates at selected N/P ratios (FIG. 4B).

An illustrative small interfering RNA according to the present invention is siVEGF, which is represented in FIG. 4A, SEQ ID NO:1, and SEQ ID NO:2, and is directed to interfering with the expression of vascular endothelial growth factor (VEGF). The sequence of siVEGF was selected according to S. Filleur et al., SiRNA-mediated inhibition of vascular endothelial growth factor severely limits tumor resistance to antiangiogenic thrombospondin-1 and slows tumor vascularization and growth, 63 Cancer Res. 3919-3922 (2003). The siVEGF can be made by methods well known in the art or can be purchased commercially.

A carrier for use in delivering a small interfering RNA according to the present invention comprises a conjugate comprising a cholesterol residue covalently coupled to oligoarginine. The oligoarginine moiety can comprise about 4 to 16 arginine residues, with about 9 arginine residues being typical. The arginine residues in the oligoarginine can be in the L form, the D form, or a mixture of L and D forms. The oligoarginine can be made according to methods well known in the art or can be purchased commercially. In an illustrative embodiment of the invention a cholesterol residue can be covalently bonded to the oligoarginine by reacting cholesterol chloroformate with oligoarginine. The chloroformate moiety comprises an activated carboxylic acid group in the form of an acid chloride, which reacts with the amino-terminal amino group of the oligoarginine to form an amide bond. The resulting conjugate comprises a cholesterol residue coupled to an oligoarginine residue through a formate residue linker.

The carrier can then be mixed with the siRNA to form a complex. The complex forms by virtue of ionic interactions between the polycationic oligoarginine and the polyanionic siRNA.

The complex can then be used for delivering the siRNA into a cell. This is accomplished in vitro by contacting selected cells with the complex. For example, a solution containing the complex is added to the growth medium of cells being grown in cell culture, and the complex and cells are permitted to remain in contact for a selected period of time. This selected period of time can easily be determined by a person of ordinary skill in the art without undue experimentation. The carrier portion of the complex causes or induces the complex, including the siRNA, to be taken into the cells. SiRNA is delivered into a cell in vivo by administering the complex to the individual to be treated, such as by subcutaneous, intramuscular, or other injection. After injection, the complex contacts cells and the complex is taken into the cells. The dosage of the complex and the frequency and number of repetitions of administration can be determined by a person of ordinary skill in the art without undue experimentation.

As an illustrative example of the present invention, a method of treating a person for cancer comprises administering a complex to a patient in need of treatment for cancer. The siRNA portion of the complex should be selected for its anticancer utility, such as an anti-VEGF siRNA. Administration of the complex results in the complex coming into contact with cancer cells. Thus, the route of administration should be selected to maximize the likelihood of the complex and the cancer cells coming into contact with each other. When the complex contacts the cancer cells, the complex is taken into the cancer cells, where the siRNA carries out its RNAi function. For example, an anti-VEGF siRNA inhibits the expression of VEGF in the treated cancer cells, thus treating the cancer.

EXAMPLES

In an illustrative embodiment of the present invention, a cholesteryl oligo D-arginine (9 residues) conjugate (Chol-R9) was synthesized as a siRNA delivery vehicle for vascular endothelial growth factor (VEGF) silencing. VEGF is a growth factor most consistently found in a wide variety of conditions associated with angiogenesis. D. W. Leung, G. Cachianes, W. J. Kuang, D. V. Goeddel & N. Ferrara, Vascular endothelial growth factor is a secreted angiogenic mitogen, 246 Science 1306-1309 (1989). It has been reported that impairing the function of VEGF could inhibit tumor growth and metastasis by preventing the tumor's vascularization in a variety of animal models. K. J. Kim et al., Inhibition of vascular endothelial growth factor-induced angiogenesis suppresses tumour growth in vivo, 362 Nature 841-844 (1993); R. A. Brekken et al., Selective inhibition of vascular endothelial growth factor (VEGF) receptor 2 (KDR/Flk-1) activity by a monoclonal anti-VEGF antibody blocks tumor growth in mice, 60 Cancer Res. 5117-5124 (2000); J. Holash et al., VEGF-Trap: a VEGF blocker with potent antitumor effects, 99 Proc. Nat'l Acad. Sci. USA 11393-11398 (2002). As described below, the potency of Chol-R9 conjugate as a siRNA delivery vehicle in vitro and in vivo in a mouse tumor model was demonstrated.

Where applicable, results are reported as means±SD. The statistical analysis between groups was determined using a nonpaired t test. $p \leq 0.05$ was considered significant.

Example 1

Synthesis of Cholesteryl Oligoarginine (Chol-R9)

Figure 1:
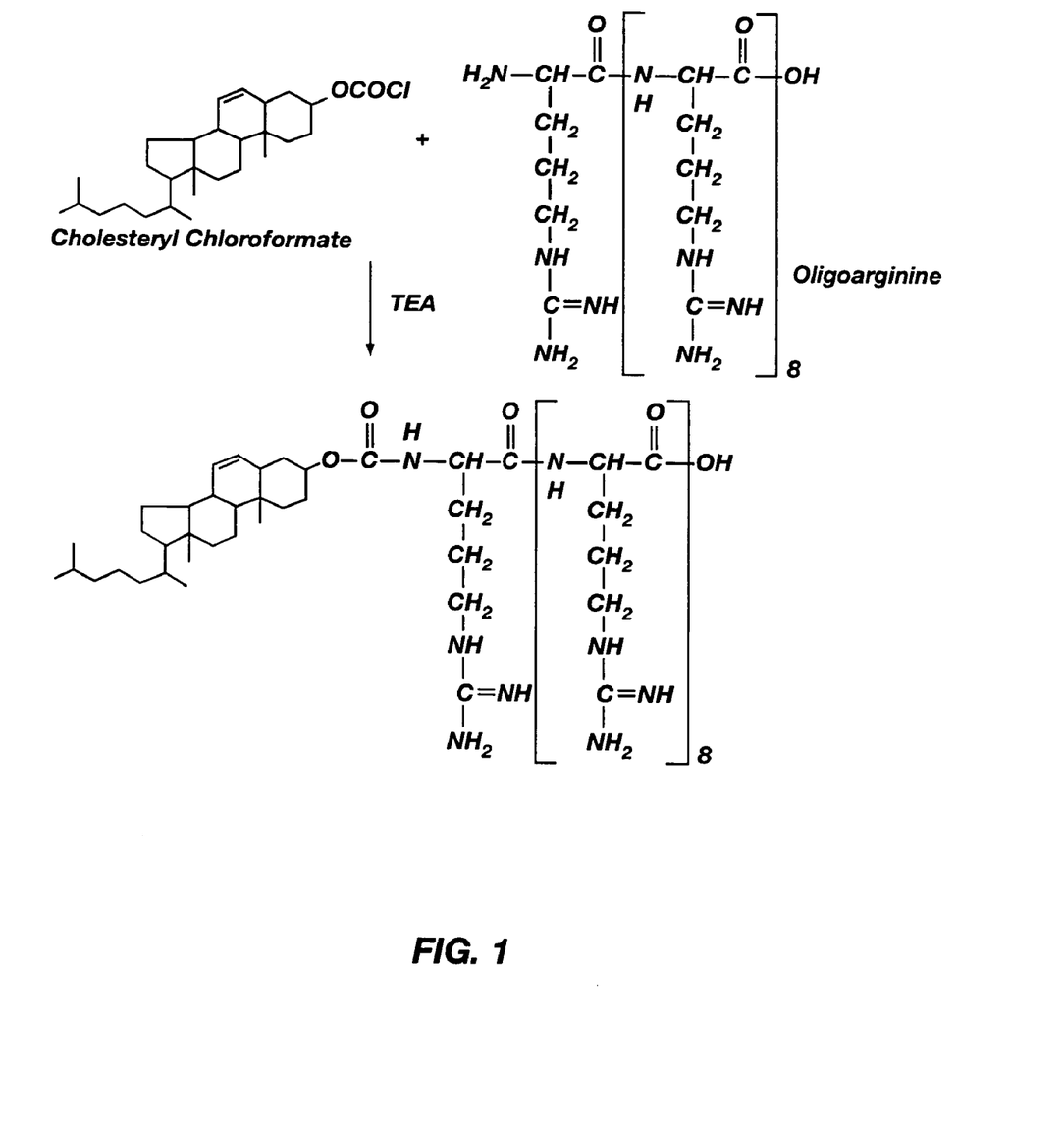
FIG. 1 is a schematic diagram showing an illustrative scheme for synthesis of a cholesteryl oligo D-arginine (9 residues) conjugate (Chol-R9).

Cholesteryl oligoarginine (Chol-R9) was synthesized by reacting cholesterol chloroformate (Aldrich Chemical Co., Milwaukee, Wis.) and oligo D-arginine (9 residues; R9) (Genemed Synthesis, Inc., San Franscisco, Calif.) in the presence of triethylamine (TEA) (FIG. 1). Oligoarginine (15.4 mg, 10.8 µmole) was dissolved in 5 ml of anhydrous dimethylformamide. After adding 15.08 µl of TEA to the oligoarginine solution, cholesterol chloroformate (24.3 mg, 54 µmole) in 5 ml of anhydrous tetrahydrofuran (THF) was slowly added at room temperature. The reaction mixture was stirred overnight. Upon completion of the reaction, solvents were removed by purging dry nitrogen gas through a glass transfer pipette. Remaining cholesterol chloroformate and TEA were removed by rinsing three times each with 15 ml of diethyl ether. The crude precipitate was dialyzed (MWCO 500, Spectrum) for two days against deionized distilled water to remove free cholesterol. Fourteen milligrams of Chol-R9 was finally collected after freeze drying.

Figure 2A:
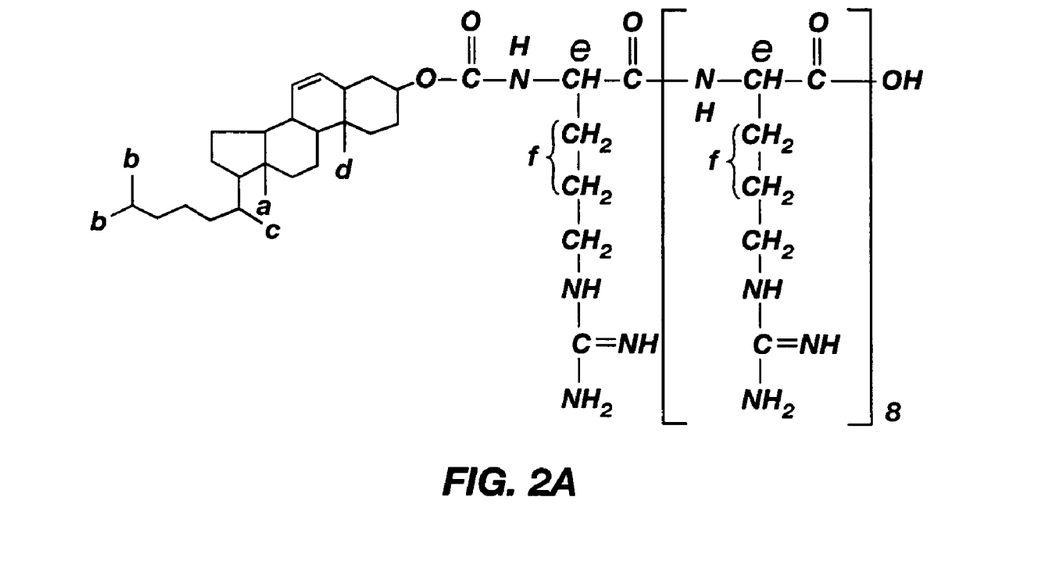
FIGS. 2A and 2B show, respectively, the structure of Chol-R9 conjugate and a $^1$H-NMR spectrum of Chol-R9, each labeled to show the correspondence between functional groups and peaks in the spectrum.
Figure 2B:
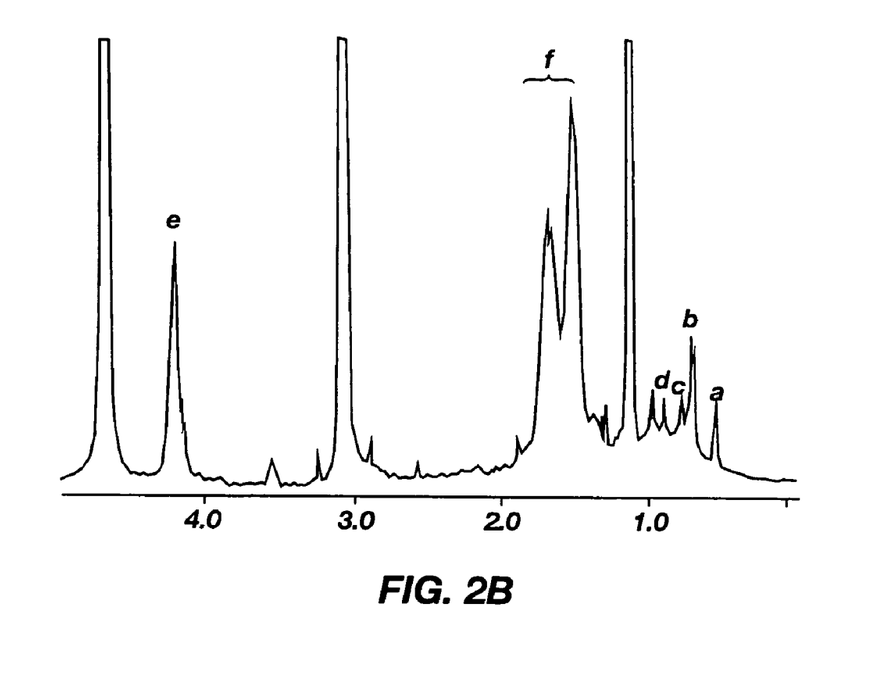
Figure 2C:
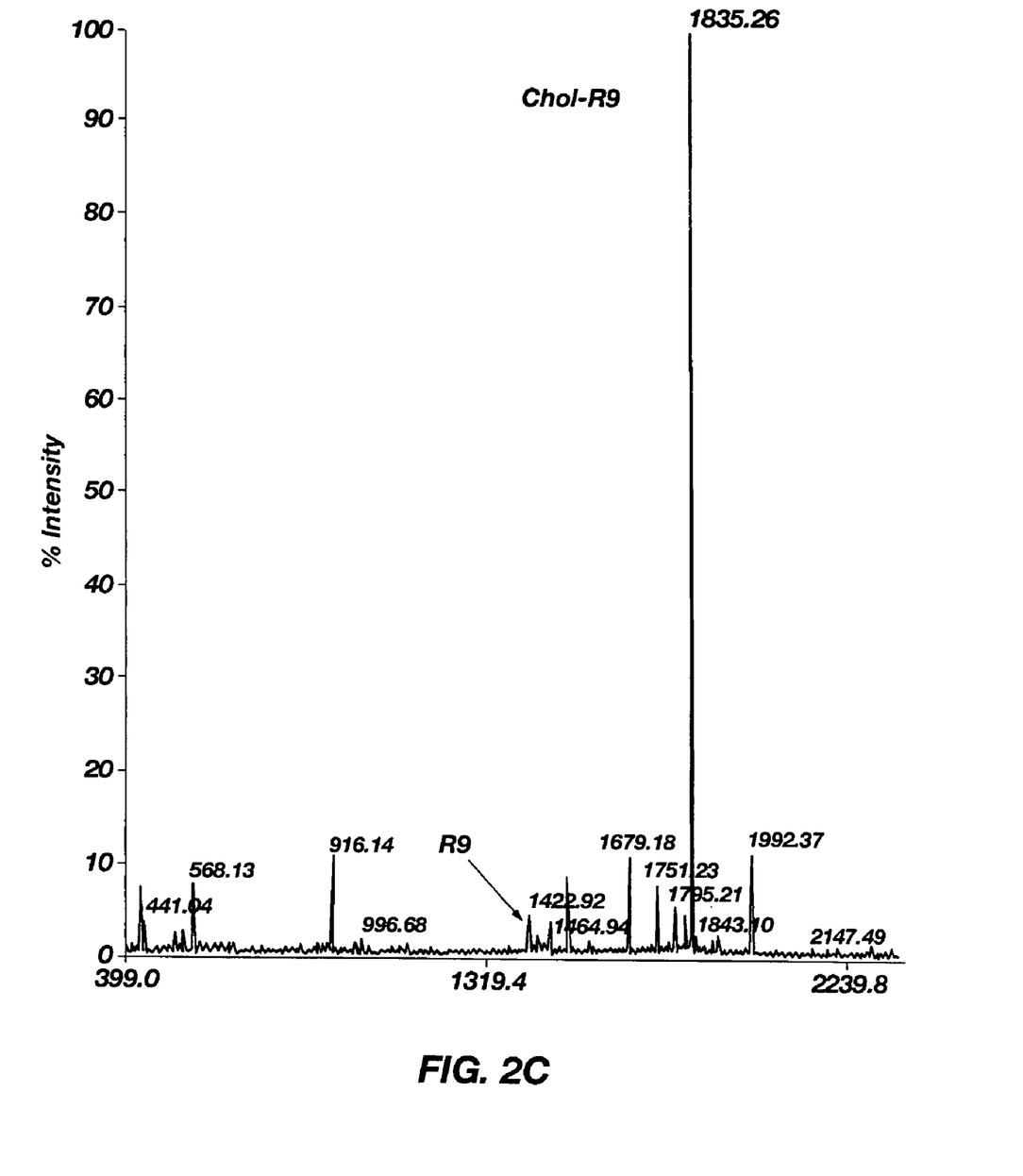
FIG. 2C shows a matrix-assisted laser desorption/ionization time of flight (MALDI-TOF) mass spectrum of Chol-R9.

Synthesized Chol-R9 was then characterized by $^1$H-NMR spectroscopy and MALDI-TOF mass spectrum analysis. The $^1$H-NMR spectrum of Chol-R9 showed characteristic cholesteryl methyl proton peaks ranging from 0.5 ppm to 1.0 ppm (FIGS. 2A and 2B). Oligoarginine (R9) proton peaks were also shown in the spectrum. Notably, the methine proton peak of R9 (protons at α-carbons), which represents 9 protons, appeared at 4.2 ppm. The coupling yield of cholesteryl chloroformate to R9 was determined from the cholesteryl methyl proton peak at 0.5 ppm, which represents 3 protons, and the proton peak of arginine α-carbon at 4.2 ppm using the following equation: Coupling yield $(\%) = (3 \times A_{0.5\ ppm}/A_{4.2\ ppm}) \times 100$, where, $A_{0.5\ ppm}$ and $A_{4.2\ ppm}$ represent integrations of proton peaks at 0.5 ppm and 4.2 ppm in the NMR spectrum of Chol-R9, respectively. The calculated coupling yield in this study was 50.3%. The mass spectrum of Chol-R9 showed a predominant peak at 1835.28 (m/z), which can be assigned as (M−H) (FIG. 2C). Impurities in the synthesized Chol-R9 were minimal.

Example 2

Complex Formation of Chol-R9 with Plasmid DNA

To identify the characteristics of Chol-R9 for acting as an efficient non-viral gene carrier, DNA complex formation was analyzed by agarose gel electrophoresis at different N/P ratios, i.e., the ratio of concentrations of total nitrogen atoms (N) of the polycation to the phosphate groups (P) of reporter plasmid DNA. Chol-R9/pCMV-luc complexes were formed at different N/P ratios by incubating in 5% glucose solution at room temperature for 30 min. Each sample was then analyzed by electrophoresis on a 1% agarose gel with ethidium bromide (EtBr, 0.1 µg/ml).

Figure 3A:
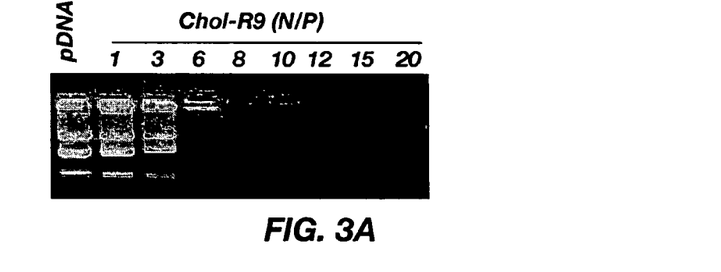
FIGS. 3A and 3B show electrophoretic patterns of carrier/plasmid DNA complexes with Chol-R9 (FIG. 3A) and R9 (FIG. 3B) at selected N/P ratios.
Figure 3B:
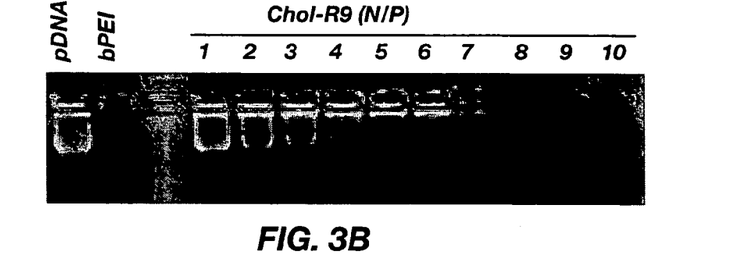

The movement of plasmid in the gel was retarded as the amount of the Chol-R9 conjugate was increased, demonstrating that the conjugate binds to negatively charged DNA, neutralizing its charge (FIG. 3A). Complete complex formations were achieved at N/P ratios at and above 8:1 (Lane 5), similar to unmodified oligoarginine (FIG. 3B).

Example 3

Cell Toxicity and In Vitro Transfection Efficiency of Chol-R9/DNA Complex

Figure 3C:
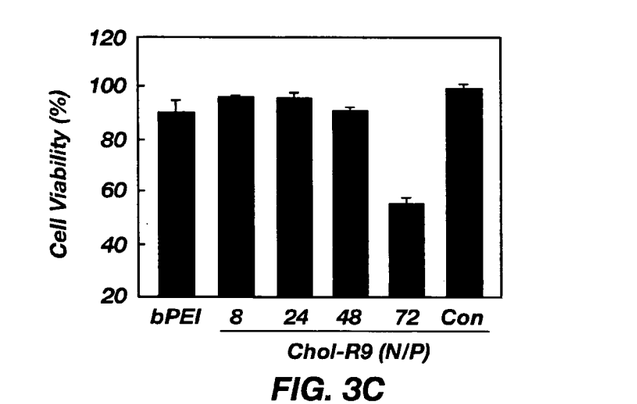
FIG. 3C shows cytotoxicity of bPEI/pCMV-Luc and Chol-R9/pCMV-Luc in mouse 293T cells at selected N/P ratios. The data are expressed as mean values±standard deviation of three experiments.

The cytotoxicity of Chol-R9/DNA complexes was investigated using a tetrazolium-based calorimetric assay according to the procedure of M. Lee, J-W. Nah, Y. Kwon, J. J. Koh, K. S. Ko & S. W. Kim, Water-Soluble and Low Molecular Weight Chitosan-Based Plasmid DNA Delivery, 18 Pharm. Res. 18: 427-431 (2001). In this test, viability of cells was assessed by the metabolism of a water-soluble tetrazolium dye, 3-(4,5-dimethylthiazol-2-yl)-2,5-diphenyltetrazolium bromide (MTT), into insoluble formazan salts (Sigma Chemical Co.) (FIG. 3C). Briefly, 293T cells were plated in 24-well plates at 60,000 cells per well and allowed to incubate for 24 h. Polymer/DNA complexes were added in triplicate to the wells at 0.5 µg reporter plasmid DNA per well at N/P ratios from 8 to 72. The bPEI (MW:25 kDa) control was prepared at a 5:1 N/P ratio. After 44 hours of incubation, cell viability was determined, where viability was compared to cells that received 5% glucose instead of polyplex dispersions. The complex of Chol-R9/DNA showed at least 90% cell viability at N/P ratios of 8 to 48.

The transfection efficiency of the synthesized Chol-R9 was evaluated in vitro using 293T cell lines. For the transfection experiments, various Chol-R9/pCMV-Luc or R9/pCMV-Luc complexes were formulated with a fixed amount (50 µg/ml) of pCMV-Luc reporter plasmid. P.-J. Chang, Y.-S. Chang & S.-T. Liu, Role of Rta in the translation of bicistronic BZLF 1 of Epstein-Barr virus, 72 J. Virol. 5128-5136 (1998). When cells reached ~80% confluency, transfections were carried out on 293T cells in 6-well plates maintained in DMEM (GIBCO) medium at 37° C. in a humidified atmosphere containing 5% $CO_2$. After 4 hours of incubation, the medium was replaced with 2 ml of fresh medium supplemented with 10% FBS (Hyclone Labs, Logan, Utah) and the cells were cultured for 48 h. Luciferase expression was quantified using the Luciferase Assay System (Promega Corp., Madison, Wis.) normalized by mg protein.

Figure 3D:
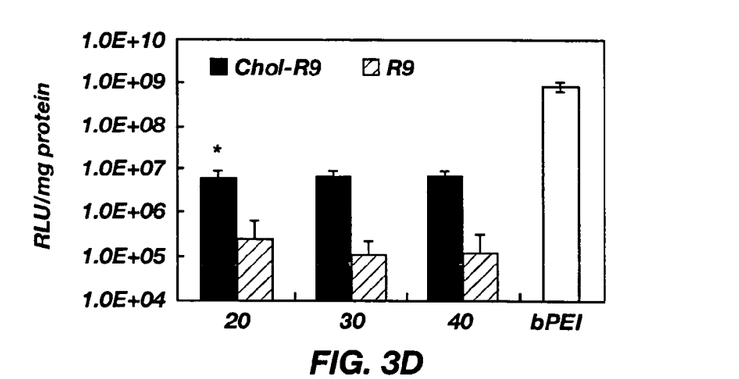
FIG. 3D shows transfection profiles at selected N/P ratios of Chol-R9/plasmid DNA complexes, R9/plasmid DNA complexes, and bPEI/plasmid DNA complexes as measured by luciferase expression. The data represent mean values±standard deviation of experiments run in triplicate. *p<0.05 compared to unmodified R9.

Chol-R9/pCMV-Luc complexes showed higher transfection efficiency than R9/pCMV-Luc complexes at N/P ratios of 20 to 40 (FIG. 3D). These results suggest that the conjugation of cholesterol to R9 provides enhanced cellular uptake of complexes and increased transfection efficiency.

Example 4

Complex Formation of Chol-R9 Conjugate with siRNA

Figure 4B:
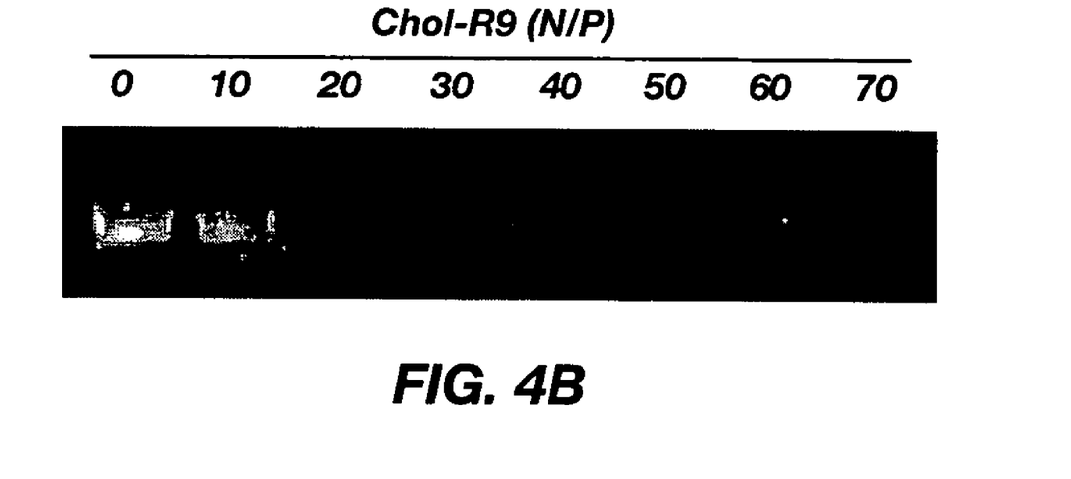

SiRNA targeting mouse VEGF (siVEGF) and scrambled siRNA (scVEGF) were purchased from Integrated DNA Technologies (Coralville, Iowa). Sequences of siRNA (SEQ ID NO:1 and SEQ ID NO:2) and scVEGF (SEQ ID NO:3 and SEQ ID NO:4) are shown in FIG. 4A. The siRNA sequences were selected according to the method of S. Filleur et al., SiRNA-mediated inhibition of vascular endothelial growth factor severely limits tumor resistance to antiangiogenic thrombospondin-1 and slows tumor vascularization and growth, 63 Cancer Res. 3919-3922 (2003). Various amount of Chol-R9, ranging from 0 ng to 44.5 ng, were added to 7 ng of siRNA at a Chol-R9/siRNA N/P ratios from 0 to 70 in 5% glucose solution and incubated for 30 min at room temperature. After incubation, each sample was electrophoresed on 13% polyacrylamide gel (w/v) for 1 h at 100 V to identify the formation of Chol-R9/siRNA complexes by gel retardation assay. TBE (89 mM Tris-borate, 2 mM EDTA) buffer was used as electrophoresis buffer. Following EtBr (0.1 µg/ml) staining, the gel was illuminated with a UV illuminator to show the location of the siRNA. The positively charged oligoarginine (R9) of Chol-R9 conjugate makes complexes with the negatively charged phosphate ions on the backbone of siRNA. When the value of N/P ratio of Chol-R9/siRNA reached 40, free siRNA was not detected on the PAGE electrophoresis (FIG. 4B).

Example 5

VEGF Silencing Effect of Chol-R9/siRNA Complex In Vitro

To evaluate the biological significance of these systems, the inhibitory activity of siRNA against the expression of VEGF in CT-26 colon adenocarcinoma cells was investigated.

CT-26 cells were seeded in 24-well tissue culture plates at $8 \times 10^4$ cells per well in 10% FBS containing RPMI 1640 medium. Cells achieved 80% confluency within 24 h, after which they were transfected with cationic substance/siRNA complexes prepared at N/P ratios ranging from 5 to 40. The total amount of siRNA loaded was maintained constant at 0.7 µg/well. The transfection was carried out in the absence of serum. The cells were allowed to incubate at 37° C. in the presence of complexes for 4 h in a $CO_2$ incubator, followed by replacement of 1 ml of RPMI 1640 containing 10% FBS. Thereafter, the cells were incubated at 37° C. for an additional 24 h. Cell supernatants were collected for analysis by ELISA of the amount of VEGF produced.

The amount of mouse VEGF produced in medium was determined using a mouse VEGF ELISA kit (R&D Systems Inc., Minneapolis, Minn.) according to the recommendation of the manufacturer. Briefly, a 96-microwell plate coated with mouse polyclonal anti-VEGF antibody was washed with wash buffer. Cell supernatant samples were diluted 1:4 in calibrator diluent, and 50 µl of the sample was placed in the designated wells. Similarly, VEGF standards ranging from 7.8 to 500 pg/ml, also diluted in calibrator diluent, were added to the microwell plates. The calibrator diluent alone was added in blank well and incubated at room temperature for 2 h. After washing four times with wash buffer, 100 µl of polyclonal antibody against VEGF conjugated to horseradish peroxidase was added and incubated at room temperature for 2 h. After washing the wells again four times, tetramethylbenzidine substrate solution was added and incubated at room temperature for 30 min. The enzymatic reaction was stopped by adding 100 µl of stop solution to the wells, and absorbance was determined by spectrophotometry at 450 nm. The VEGF concentration in the cell supernatant samples was calculated based on the standard curve.

Figure 5A:
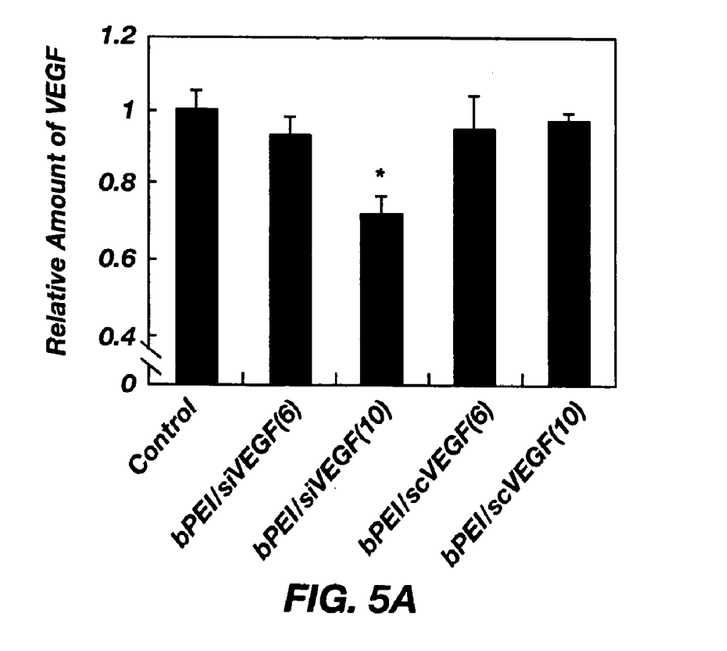
FIG. 5A shows relative amounts of VEGF, as determined by ELISA, in cells transfected with bPEI/siVEGF and bPEI/scVEGF at N/P ratios of 5 and 10.
Figure 5B:
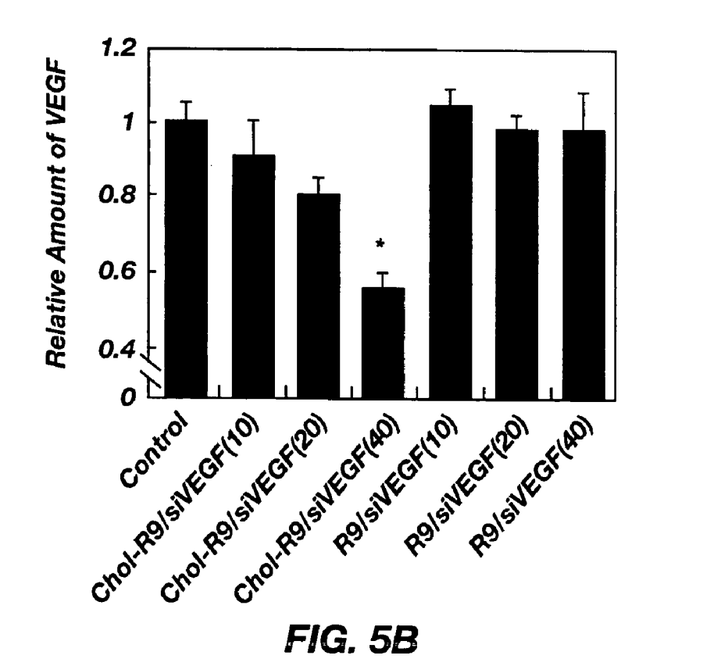
FIG. 5B shows relative amounts of VEGF in cells transfected with Chol-R9/siVEGF and R9/siVEGF at N/P ratios of 10, 20, and 40. *p<0.02 compared to non-treated control.
Figure 6A:
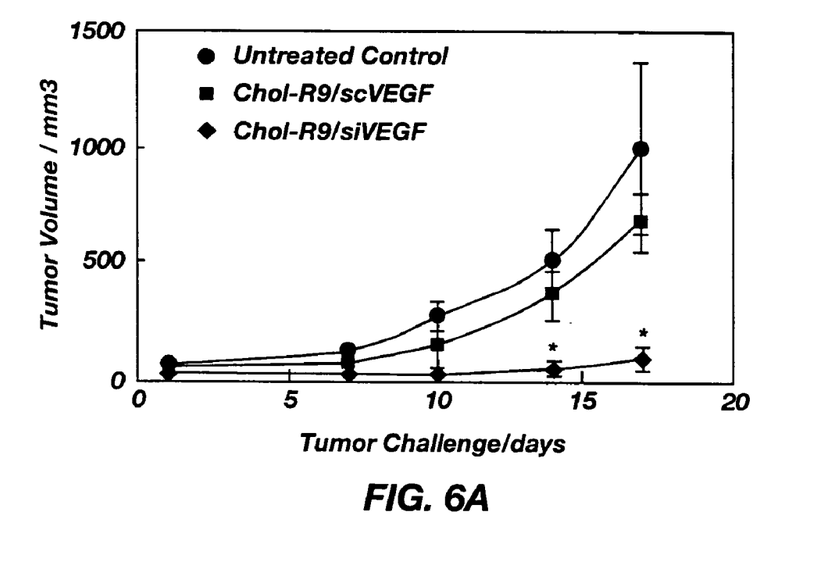
FIG. 6A shows the antitumor effect of siRNAs in vivo expressed as tumor volume ($mm^3$) as a function of the number of days since tumor challenge: (●) untreated control; (■) Chol-R9/scVEGF; (♦) Chol-R9/siVEGF. Results represent the means±standard deviation (n=5 tumors). * P<0.05 compared to Chol-R9/scVEGF.
Figure 6B:
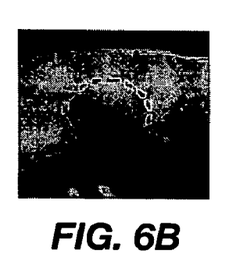
FIGS. 6B-E show images of CT-26 allografts on days 1 (FIGS. 6B and 6D) and 17 (FIGS. 6C and 6E) after treatment with Chol-R9/siVEGF (FIGS. 6b and 6C) or Chol-R9/scVEGF (FIGS. 6D and 6E).
Figure 6C:
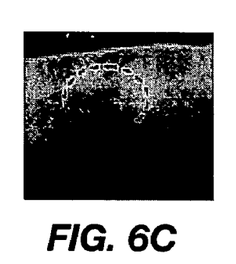
Figure 6D:
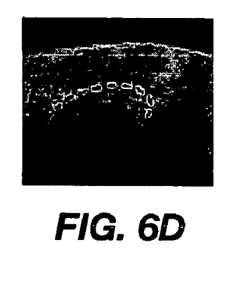
Figure 6E:
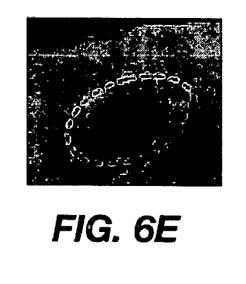

The inhibitory effect was evaluated from the relative silencing of the VEGF assayed by ELISA. As shown in FIG. 5A, appreciable silencing of VEGF expression was observed with bPEI/siVEGF complexes at an N/P ratio of 10, while scrambled scVEGF showed no effect. As shown in FIG. 5B, Chol-R9/siVEGF complexes suppressed VEGF production by 55% compared with the untreated control, whereas R9/siVEGF complexes did not silence the expression of VEGF with the same amount of siRNA.

Example 6

Inhibition of Tumor Growth with Chol-R9/siRNA Complex In Vivo

To generate tumors, 4-5 week-old female BALB/c mice were injected subcutaneously in the middle of the right flank with 100 µl of a single cell suspension containing $1 \times 10^6$ CT-26 cells. Tumor size was measured using a vernier caliper across its longest (a) and shortest diameters (b) and its volume was calculated using the formula $V=0.5ab^2$. Treatment of the tumors was started after 10-15 days when the tumor size reached approximately 70 $mm^3$. Thus, day 1 corresponded to the start of antitumor treatment. Chol-R9/siVEGF and Chol-R9/scVEGF complexes (N/P ratio of 40:1) were prepared in 5% glucose, and 50 µl of the complexes was injected subcutaneously directly into the tumors at a dose of 3.5 µg siRNA/ mouse. As controls, 5% glucose solutions were injected. Injections were repeated every four days for a total of 6 injections. The tumors were measured every 4 days and mice were examined for appearance and growth or necrosis, as well as decreased physical activity. Tumor progression was reported in terms of tumor volume over a period of 2 weeks.

Figure 7A:
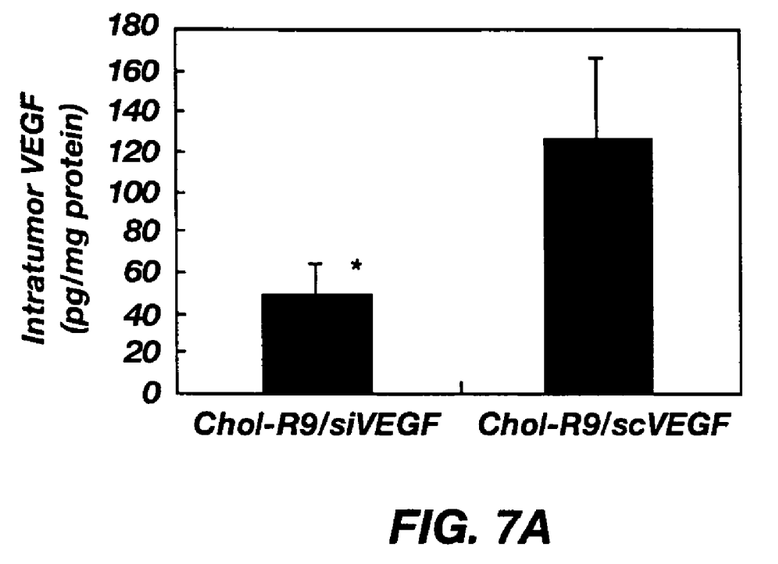
FIG. 7A shows intratumoral VEGF levels, as measured by ELISA, in tumors at 17 days after injection with Chol-R9/siVEGF or Chol-R9/scVEGF.
Figure 7B:
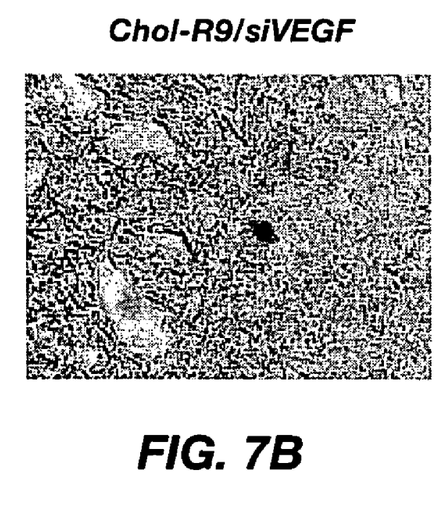
FIGS. 7B and 7C show intratumoral vascularization by immunohistochemical staining of the subcutaneous tumors with CD 31 antibody after treatment with Chol-R9/siVEGF (FIG. 7B) or Chol-R9/scVEGF (FIG. 7C).
Figure 7C:
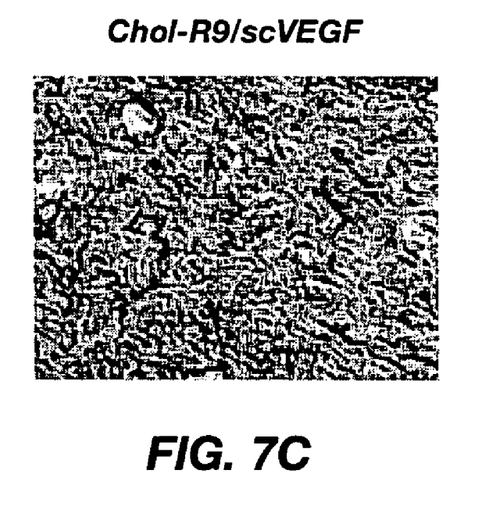

As shown in FIGS. 6A-6E, Chol-R9/siVEGF complexes markedly suppressed tumor growth compared with Chol-R9/ scVEGF complexes (p<0.05) or 5% glucose controls. To assess the relationship between the therapeutic effects by Chol-R9/siRNA and VEGF in tumors, the amount of VEGF in tumors was quantified. Tumors were excised and homogenized in PBS with protease inhibitor (Sigma Chemical Co.) and then centrifuged. The amount of VEGF in each supernatant was measured by ELISA. A dramatically lower level of VEGF in tumors treated with Chol-R9/siVEGF was observed at 17 days after the first injection, whereas the tumors treated with Chol-R9/scVEGF showed higher levels of VEGF (FIG. 7A). Next, the vascularization in tumors was examined by immunostaining with an anti-CD 31 antibody. The vascularization in tumors observed in the Chol-R9/siVEGF treated group was significantly reduced compared with tumors from the Chol-R9/scVEGF treated group (FIGS. 7B and 7C). Based on these observations, it appears that the anti-tumor effect of Chol-R9/siVEGF was mainly due to the anti-angiogenic effect of Chol-R9/siVEGF, which was confirmed by VEGF quantification (FIG. 7A) and histological examination (FIGS. 7B and 7C).

The subject matter claimed is:

1. A method of making a complex, the method comprising mixing a small interfering RNA with a conjugate comprising a cholesterol residue covalently bonded to oligoarginine through a formate residue linker, thereby forming the complex, wherein the conjugate is represented by the formula:

$$\text{cholesterol-O}-\overset{O}{\underset{\|}{C}}-\left[\overset{H}{\underset{}{N}}-\underset{\underset{\underset{\underset{\underset{\underset{NH_2}{|}}{\underset{C=NH}{|}}}{\underset{NH}{|}}}{\underset{CH_2}{|}}}{\underset{CH_2}{|}}}{\underset{CH_2}{|}}{CH}-\overset{O}{\underset{\|}{C}}\right]_n-\text{OH}$$

wherein n is about 4 to 16.

2. The method of claim 1 wherein the small interfering RNA is targeted to vascular endothelial growth factor.

3. The method of claim 2 wherein the small interfering RNA comprises siVEGF (SEQ ID NO:1 and SEQ ID NO:2).

4. The method of claim 1 wherein the oligoarginine comprises arginine residues, each of which is in the D form.

5. A composition comprising a mixture of a small interfering RNA and a conjugate comprising a cholesterol residue covalently bonded to oligoarginine through a formate residue linker, wherein the conjugate is represented by the formula:

wherein n is about 4 to 16.

6. The composition of claim 5 wherein the arginine residues are in the D form.

7. The composition of claim 5 wherein the small interfering RNA is targeted to vascular endothelial growth factor.

8. The composition of claim 5 wherein the mixture comprises a complex of the small interfering RNA and the conjugate.

9. The composition of claim 5 wherein n is about 9.

10. The method of claim 1 wherein n is about 9.

11. The composition of claim 7 wherein the small interfering RNA comprises siVEGF (SEQ ID NO:1 and SEQ ID NO:2).

* * * * *